(12) United States Patent
Eick

(10) Patent No.: US 7,008,417 B2
(45) Date of Patent: Mar. 7, 2006

(54) DETECTING COAGULUM FORMATION

(75) Inventor: Olaf Eick, Willich (DE)

(73) Assignee: Medtronics, Inc., Minneapolis, MN (US)

(*) Notice: Subject to any disclaimer, the term of this patent is extended or adjusted under 35 U.S.C. 154(b) by 258 days.

(21) Appl. No.: 10/126,604

(22) Filed: Apr. 22, 2002

(65) Prior Publication Data

US 2003/0199864 A1 Oct. 23, 2003

(51) Int. Cl.
*A61B 18/18* (2006.01)

(52) U.S. Cl. ............................................. 606/41
(58) Field of Classification Search ............. 606/27–52; 128/898
See application file for complete search history.

(56) References Cited

U.S. PATENT DOCUMENTS

| | | | | |
|---|---|---|---|---|
| 4,960,109 A | * | 10/1990 | Lele | ........................... 600/549 |
| 5,318,525 A | | 6/1994 | West et al. | |
| 5,423,808 A | * | 6/1995 | Edwards et al. | ............... 606/34 |
| 5,487,757 A | | 1/1996 | Truchai et al. | |
| 5,707,369 A | * | 1/1998 | Vaitekunas et al. | ........... 606/31 |
| 5,755,715 A | | 5/1998 | Stern et al. | |
| 5,779,699 A | | 7/1998 | Lipson | |
| 5,837,001 A | | 11/1998 | Mackey | |
| 5,843,075 A | | 12/1998 | Taylor | |
| 5,931,835 A | | 8/1999 | Mackey | |
| 5,971,980 A | | 10/1999 | Sherman | |
| 6,033,398 A | * | 3/2000 | Farley et al. | ................. 606/27 |
| 6,063,078 A | | 5/2000 | Wittkampf | |
| 6,179,832 B1 | * | 1/2001 | Jones et al. | ................... 606/32 |
| 6,409,722 B1 | * | 6/2002 | Hoey et al. | ................... 606/34 |

OTHER PUBLICATIONS

"Control of Radiofrequency Lesion Size by Power Regulation", Cirulation, vol. 80, No. 4, pp. 962–8 Oct. 1989.

* cited by examiner

*Primary Examiner*—Michael Peffley
*Assistant Examiner*—Pete Vrettakos
(74) *Attorney, Agent, or Firm*—Paul H. McDowall; Daniel G. Chapin; Girma Wolde-Michael (57) ABSTRACT

Techniques for detecting coagulum formation on an ablation electrode make use of an ablation electrode that is connected to a radio-frequency (RF) generator capable of applying a small amount of RF energy that is not cell destructive. The temperature at the ablation electrode can be precisely measured using a thermosensor incorporated within the ablation electrode. Before and after actual ablation, a low, non-cell destructing (non-ablating) amount of RF energy is generated at the ablation electrode. If no coagulum has formed during actual ablation, the temperature increase during this test application will be similar before and after the ablation attempt. If coagulum has formed during the actual ablation, however, the temperature increase during the test application after ablation will be significantly higher.

25 Claims, 5 Drawing Sheets

DETECTING COAGULUM FORMATION

FIELD OF THE INVENTION

This invention relates generally to the field of devices for cardiac surgery, and, more specifically, to devices for radio frequency (RF) ablation of cardiac tissue.

BACKGROUND

Atrial fibrillation and arrhythmias are frequently caused by the presence of an arrhythmogenic substrate, such as ectopic foci, or an accessory atrioventricular pathway. Therapies have been developed for treating atrial fibrillation and arrhythmias by destroying cardiac tissue containing the arrhythmogenic substrate or accessory pathway responsible for the atrial fibrillation or arrhythmia. A variety of approaches have been taken, including application of electrical energy or other forms of energy to destroy the undesired cardiac tissue. As examples, ablation of cardiac tissue has been accomplished by application of radio frequency electrical current, microwave energy, heat, electrical pulses, ultrasound, cryothermy, and lasers to the tissue. At present, ablation using RF energy is perhaps the most widely practiced in the context of ablation procedures that can be carried out by a catheter inserted into the closed heart.

RF catheter ablation is generally performed after an initial mapping procedure where the locations of the arrhythmogenic substrates or accessory pathways are determined. After mapping, a catheter having a suitable electrode is introduced to the appropriate chamber and manipulated so that the electrode lies proximate the cardiac tissue to be ablated. RF energy is then applied through the electrode to the cardiac tissue in order to ablate a region of the tissue that forms part of the arrhythmogenic substrate or accessory pathway. By successfully destroying that tissue, the arrhythmogenic substrate or accessory pathway is destroyed so that the abnormal signaling patterns responsible for the atrial fibrillation or arrhythmia will no longer occur.

The RF energy delivered through the electrode causes tissue in contact with the electrode to heat through resistance of the tissue to the induced electrical current. Proper heating of the tissue causes ablation. Heating of the tissue and surrounding blood beyond a certain temperature, however, can cause desiccation or charring of the tissue, catheter adhesion to the charred tissue, and emboli development within the surrounding blood. All of these problems associated with overheating of the tissue and surrounding blood at the ablation site increase the risk of complication or death to the patient.

Additionally, blood and tissue overheating may cause a coagulum to form around the RF electrode. This coagulum greatly increases the impedance between the RF electrode and the return electrode, and proportionately reduces the RF energy delivered to the target tissue. RF energy that is delivered to the target tissue via the coagulum is insufficient to cause heating or ablation. Therefore, when a coagulum forms it must be detected so that the catheter can be removed from the patient and the coagulum cleaned off the electrode. If the coagulum is not detected, the procedure may fail to adequately destroy the arrhythmogenic substrate or accessory pathway that is the cause of the atrial fibrillation or arrhythmia.

One response to the problems caused by blood and tissue overheating has been the inclusion of a temperature sensor within the RF electrode, in conjunction with feedback control of the RF signal to maintain the blood and tissue temperature at a set level. The set level typically is below the temperature at which overheating is believed to occur. For example, U.S. Pat. No. 5,837,001 discloses a feedback network that controls the gain of an RF amplifier based on a comparison of the signal received from a temperature sensor to a preset temperature value.

Unfortunately, despite temperature controlled ablation, blood and tissue overheating still occurs during some RF catheter ablation procedures. Further, temperature controlled ablation does not detect coagulum formation. When a coagulum forms around an electrode, any subsequent RF applications result in heating of the coagulum, which in turn heats the RF electrode and the included thermocouple. During temperature controlled ablation, this leads to the maintenance of a high temperature with relatively low RF power output. High electrode temperature with relatively low RF power output is as indicative of good electrode-tissue contact and sufficient heating, as it is of coagulum formation, making the distinction difficult.

In realization that coagulum formation increases the impedance between the RF electrode and the return electrode, some existing techniques for detecting coagulum formation involve monitoring of the measured impedance. According to these techniques, if the impedance value exceeds a predetermined range, or increases at greater than a predetermined rate, an alarm may be communicated to the operator or RF power to the electrode may be reduced or suspended. In either case, the operator will be alerted to the need to remove the catheter and remove the coagulum.

Unfortunately, this method of coagulum detection may not be reliable. For example, if the coagulum is soft, the electrical properties are similar to the blood. The formation of a soft coagulum will not appreciably change the measured impedance, and will not be detected by the method of these references.

Further, coagulum detection may not reliably detect a coagulum early in the coagulum formation process. It is desirable to detect a coagulum early in the formation process. Occasionally, when the physician or technician removes the catheter to check for the presence of a coagulum or remove coagulum from the electrode, the coagulum breaks off of the electrode as the catheter is being removed from the patient. This broken-off coagulum may become an embolus, and poses a serious risk to the patient. The larger the coagulum is allowed to become, the greater the risk to the patient.

Commonly assigned U.S. Pat. No. 6,036,078, issued to Wittkampf, discloses a system and method for determining the degree to which the electrode is in contact with the cardiac tissue. In general, Wittkampf describes the repeated application of RF energy of low, non cell destructing power, and the monitoring of the temperature response at the electrode to the energy application. The temperature at the electrode in response to the energy application will be proportionately higher depending on the degree of electrode contact with the cardiac tissue.

Therefore, there is a need in the art for a system and method for reliably detecting the formation of a coagulum on an electrode during ablation. Further, there is a need in the art for a system and method for reliably detecting the formation of a coagulum on an electrode early in coagulum formation process.

Examples of RF ablation techniques and devices, including those employing temperature controlled ablation, impedance monitoring, and other methods for detecting or avoiding coagulum formation, may be found in the issued U.S. Patents listed in Table 1 below.

TABLE 1

| U.S. Pat. No. | Inventor | Issue Date |
|---|---|---|
| 6,063,078 | Wittkampf | May 16, 2000 |
| 5,971,980 | Sherman | Oct. 26, 1999 |
| 5,957,961 | Maguire, et al. | Sep. 28, 1999 |
| 5,931,835 | Mackey | Aug. 3, 1999 |
| 5,843,075 | Taylor | Dec. 1, 1998 |
| 5,837,001 | Mackey | Nov. 17, 1998 |
| 5,779,699 | Lipson | Jul. 14, 1998 |
| 5,755,715 | Stern, et al. | May 26, 1998 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to the detection of coagulum formation in prior art RF catheter ablation systems. Such problems may include, for example, inability to reliably detect coagulum formation with existing techniques. It is an object of the present invention to provide a system and method for detecting coagulum formation with increased reliability. It is a further object of the present invention to provide a system and method for detecting coagulum formation early in the coagulum formation process. In particular, it is an object of the present invention to detect whether a coagulum has formed on an electrode during ablation by measuring, both before and after actual ablation, the temperature response at the electrode to the delivery of an amount of RF energy which is non-damaging to the cellular structures of human body tissue. Various embodiments of the present invention may have the object of solving at least one of the foregoing problems.

The present invention has certain features. In particular, various embodiments of the present invention may have one or more of the following features: an electrode for delivering RF energy from an RF generator to cardiac tissue, and a temperature sensor, proximate to or within the electrode, for measuring the temperature at the electrode. The present invention also includes a circuit, which is coupled to the RF generator, the temperature sensor, and a user interface.

In order to detect the formation of a coagulum on the electrode during ablation, the present invention compares temperatures measured by the temperature sensor before and after ablation. Before ablation, the electrode delivers an amount of RF energy which is non-damaging to the cellular structures of human body tissue, perhaps in the form of a pulse, and the temperature sensor measures the temperature response at the electrode to the delivered energy.

After ablation, the electrode again delivers the same amount and form of RF energy, and the temperature sensor again measures the temperature response at the electrode to the delivered energy. If a coagulum has formed on the electrode during ablation, the temperature at the electrode will increase more quickly, reach a higher peak temperature, and cool more slowly in response to the delivered energy.

The present invention therefore features a circuit that directs the delivery of energy by the electrode, receives the temperatures measured by the temperature sensor in response to the delivered energy, and compares the temperature responses to determine if a coagulum has formed during ablation. The circuit also generates an appropriate output to notify the user whether a coagulum has formed.

The present invention has certain advantages. That is, in comparison to known implementations for detecting coagulum formation, various embodiments of the present invention may provide one or more advantages. Such advantages may include, for example, more reliable detection of the formation of a coagulum on an electrode during ablation and more reliable detection of the formation of a coagulum on an electrode early in coagulum formation process. Consequently, the invention can help avoid both ablation procedures that fail to adequately destroy the arrhythmogenic substrate or accessory pathway that is the cause of the atrial fibrillation or arrhythmia, and the formation of large coagulum that can break off of the electrode and embolize.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

Figure 1:
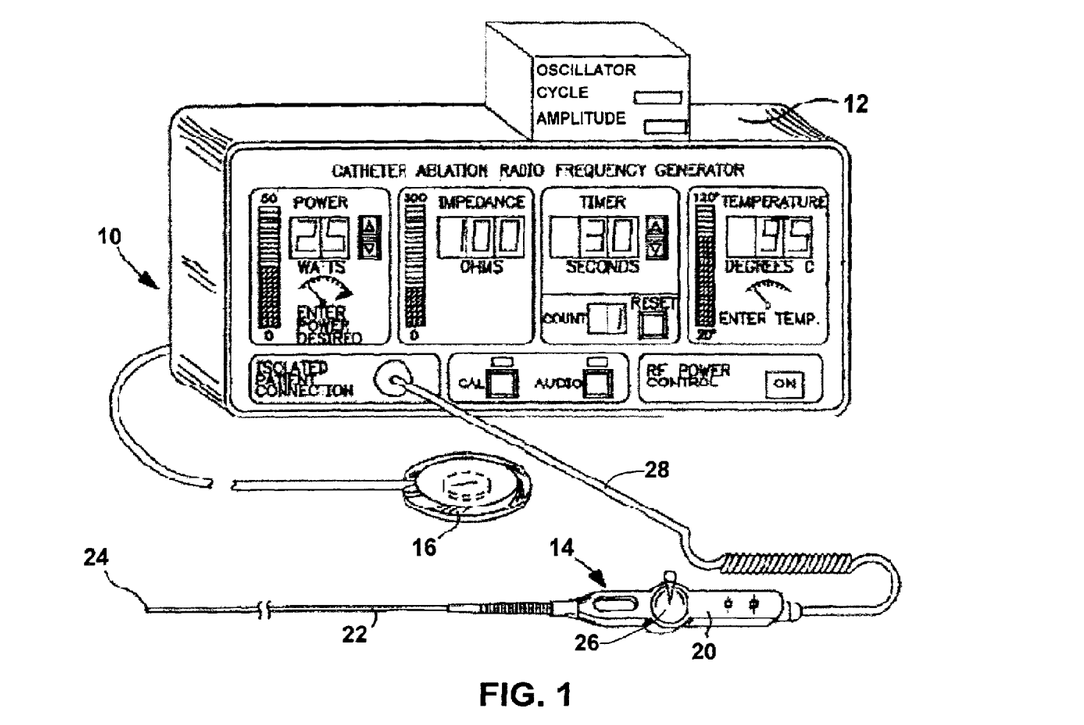
FIG. 1 shows a system for performing ablation on human tissue that embodies exemplary features of the invention.

FIG. 1 shows a system 10 for performing ablation on human tissue. System 10 may embody certain features of the invention. In particular, system 10 includes a radio frequency generator 12 that delivers radio frequency energy ("RF energy"). Other types of energy may also be used, such as microwave energy, heat, electrical pulses, ultrasound, cryothermy, and lasers. The specific type of energy delivered is not essential to the invention. System 10 also includes a steerable catheter 14 carrying a radio frequency emitting ablation electrode 30 (shown in FIG. 2). As will be described, in accordance with the invention, system 10 can be configured to detect whether a coagulum has formed on electrode 30 by sensing temperature during or after application of a low level RF energy pulse before and after an actual ablation procedure.

As shown in FIG. 1, system 10 may operate in a monopolar mode. In this arrangement, system 10 includes a skin patch electrode that serves as an indifferent second electrode 16. In use, indifferent electrode 16 attaches to the patient's back or other exterior skin area. Alternatively, system 10 can be operated in a bipolar mode. In this mode, catheter 14 carries two or more electrodes.

System 10 can be used in many different environments. For purposes of illustration, system 10 will be described herein in the context of cardiac ablation therapy.

For cardiac ablation therapy, a physician steers catheter 14 through a main vein or artery (typically the femoral vein or artery) into the interior region of the heart that is to be treated. The physician then further manipulates catheter 14 to place ablation electrode 30 into contact with the tissue within the heart that is targeted for ablation. Imaging techniques, such as fluoroscopy, ultrasound, or MRI imaging may aid the physician in guiding catheter 14 to the appropriate location. RF energy is delivered from RF generator 12 to ablation electrode 30 to form a lesion on the contacted tissue.

As shown in FIG. 1, catheter 14 may include a handle 20, a guide tube 22, and a tip 24, which carries the ablation electrode 30. Handle 20 encloses a steering mechanism 26 for the catheter tip 24. A cable 28 extending from the rear of the handle 20 has a plug (not shown). The plug connects the catheter 14 to the generator 12 for conveying RF energy to the ablation electrode 30. The RF energy heats the tissue to form the lesion.

Figure 2:
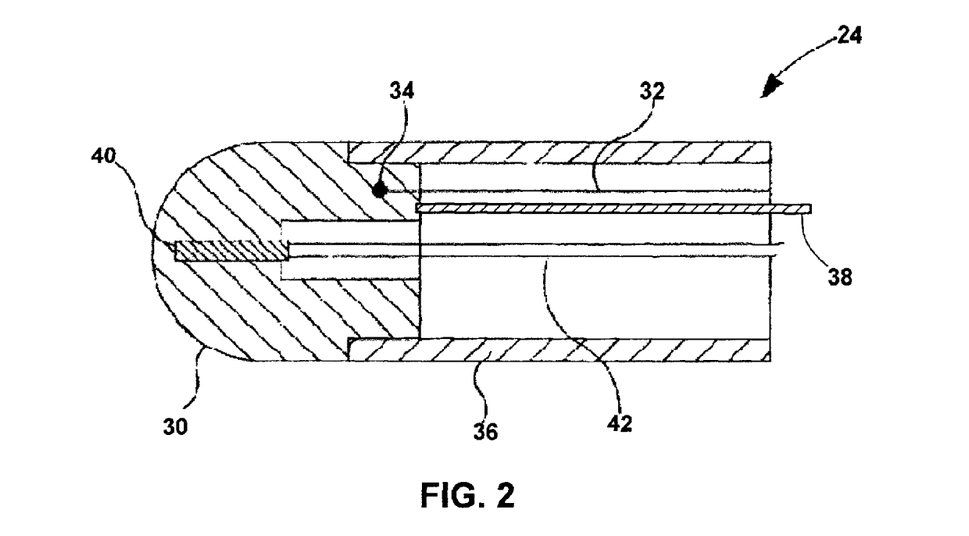
FIG. 2 is a cross-sectional side view of the distal end or tip of the catheter of FIG. 1.

One or more steering wires 32 (shown in FIG. 2) extend through guide tube 22 to interconnect steering mechanism 26 to the left and right sides of tip 24 at one or more fixation points 34 (shown in FIG. 2). Rotating steering mechanism 26 to the left pulls on the left steering wire, causing tip 24 having ablation electrode 30 to bend to the left. Rotating steering mechanism 26 to the right pulls on the right steering wire, causing the catheter tip 24 to bend to the right. In this way, the physician steers the ablation electrode 30 into contact with the tissue to be ablated. Steering mechanism 26 may, in some embodiments of the present invention, correspond to the steering mechanisms disclosed in U.S. Pat. No. 5,318,525, issued Jun. 7, 1994 to West, et al., or U.S. Pat. No. 5,487,757, issued Jan. 30, 1996 to Truckai, et al., both of which are incorporated herein by reference in their entirety.

RF generator 12 includes a radio frequency power source connected through a main isolation transformer to first and second conducting lines (not shown). In the illustrated embodiment, the power source may deliver between 0–100 Watts of power at a frequency between 100 kHz–1 MHz. The first conducting line leads to ablation electrode 30. The second conducting line leads to the indifferent electrode 16.

FIG. 2 is a sectional view of the distal end or tip 24 of the catheter 14 seen in FIG. 1. Catheter tip 24 has ablation electrode 30 mounted on catheter shaft 36. Ablation electrode 30 is electrically coupled to the RF generator 12 through conductor 38. Positioned within electrode 30 is temperature sensor assembly 40. Temperature sensor assembly 40 may include, for example, a thermistor or a thermocouple. Although shown within electrode 30, temperature sensor assembly 40 may also be positioned on, adjacent to or separated from electrode 30. A pair of temperature sensor assembly leads 42 couple the temperature sensor assembly 40 to the RF generator 12. Temperature sensor assembly 40 is used to sense the temperature at the ablation electrode 30. Temperature sensor assembly may generate temperature signals itself, or may generate temperature signals by modulating signals conducted through temperature sensor assembly leads 42 as a function of the sensed temperature. As discussed in more detail below, whether or not a coagulum has formed on the ablation electrode 30 during ablation may be determined by sensing the difference between the temperature response at the ablation electrode 30 to a low level RF energy pulse before and after actual ablation.

Figure 3:
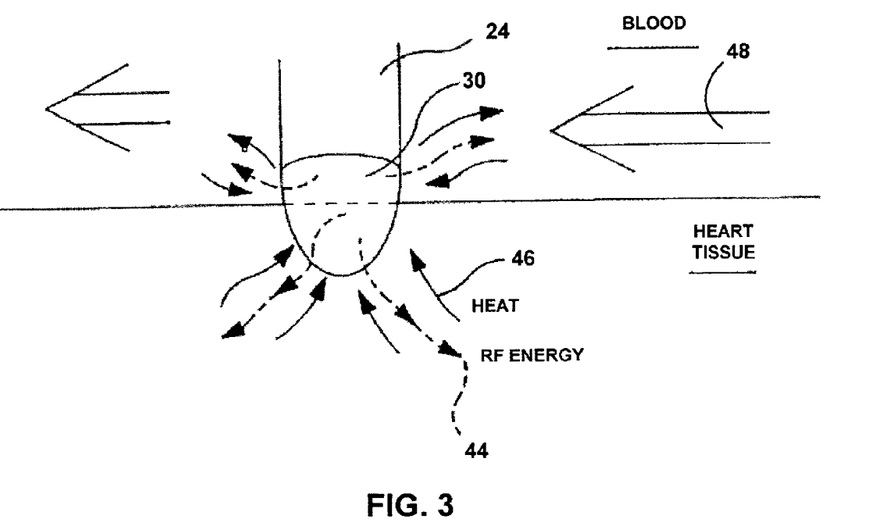
FIG. 3 illustrates a catheter tip having an electrode that is free of coagulum.

FIG. 3 illustrates a catheter tip 24 having an ablation electrode 30 that is emitting RF energy into the blood stream and the cardiac tissue, and the transmission of heat back into the catheter tip. As discussed above, during RF ablation, high frequency current is delivered to the tissue and fluids that contact the ablation electrode 30. Because these tissues and fluids have some electrical resistivity, heat is generated within the tissues and fluids. This so-called resistive heating thereby causes energy in the form of heat to be transmitted back into the ablation electrode 30. As seen, RF energy represented by dotted lines 44 is emitted from the ablation electrode 30. In return, heat, represented by solid lines 46, is created in the surrounding tissues and fluids, in this case cardiac tissues and the blood stream, and is partially radiated back into the ablation electrode 30. Thus, the delivery of RF energy to the tissues or fluids of the body causes the ablation electrode 30 to heat.

Figure 4:
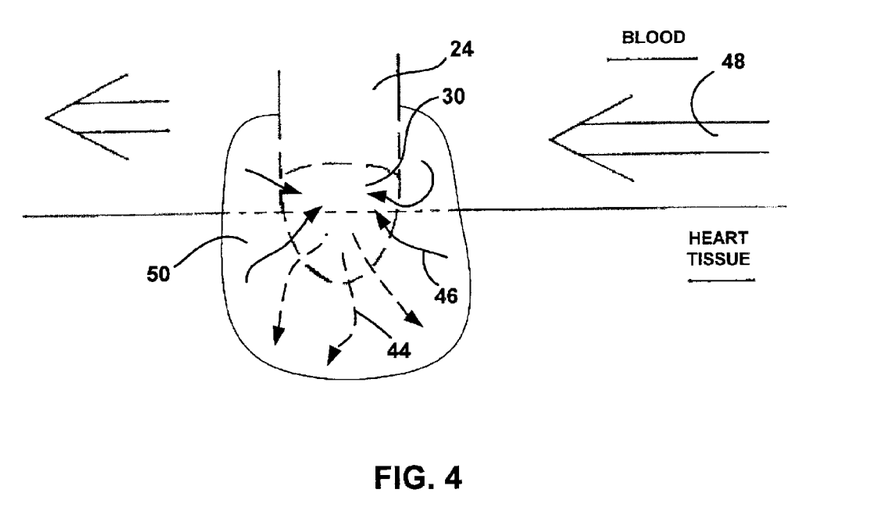
FIG. 4 illustrates a catheter tip having an electrode that is covered with a coagulum.

FIG. 4 illustrates a catheter tip 24 where a coagulum 50 has formed around the ablation electrode 30. Upon formation of the coagulum, RF energy 44 from the ablation electrode 30 no longer reaches the cardiac tissue, but is instead partially or completely absorbed by coagulum 50. Therefore, further ablation attempts may range from less effective to entirely ineffective. As was the case with the cardiac tissue and blood in FIG. 3, heat 46 is generated within the coagulum 50 and transmitted back to the ablation electrode 30. Unlike the case in FIG. 3, however, no RF energy is absorbed and carried away by the blood flow 48. Further, the electrode 30 of FIG. 4 is not exposed to the convective cooling of the blood flow 48. Therefore, the heat 46 resulting from the RF energy 44 is more completely radiated back into the ablation electrode 30 by the coagulum 50.

The present invention makes use of the realization that a coagulum tends to radiate heat back into and prevent convective cooling of ablation electrode 30 to detect coagulum formation around an ablation electrode. The electrode may deliver the same amount of RF energy before and after an actual ablation procedure. An amount of RF energy which is non-damaging to the cellular structures of human body tissue may be selected. This amount may, for example, be between approximately 0.1 and 1.0 Watts. In Wittkampf, et. al, "Control of Radiofrequency Lesion Size by Power Regulation," Circulation, vol. 80, no. 4, pp. 962–8, Oct. 1989, it was reported that permanent tissue effects occur when RF energy is delivered at 1.8 Watts for 5 seconds or at 0.7 Watts for 60 seconds. This amount of RF energy can, for example, be delivered as a pulse, which may be referred to herein as a test pulse.

If no coagulum has formed around ablation electrode 30 during actual ablation, the temperature responses at the electrode to the test pulse before and after ablation will be similar. If, on the other hand, a coagulum has formed around the ablation electrode, the temperature at the electrode will increase more quickly, reach a higher peak temperature, and cool more slowly in response to the test pulse delivered after the ablation procedure. This difference in temperature response at the ablation electrode in the presence or absence of a coagulum has been demonstrated experimentally to be significant, and can be used to detect coagulum formation. For example, in response to a 0.3 Watt pulse that was 10 seconds long, the peak temperature increase was 0.05° C. in the absence of coagulum, and 0.90° C. when coagulum was present. If significant coagulum formation is detected, system 10 may alert the physician, who may elect to remove the catheter and remove the coagulum from the electrode.

Figure 5:
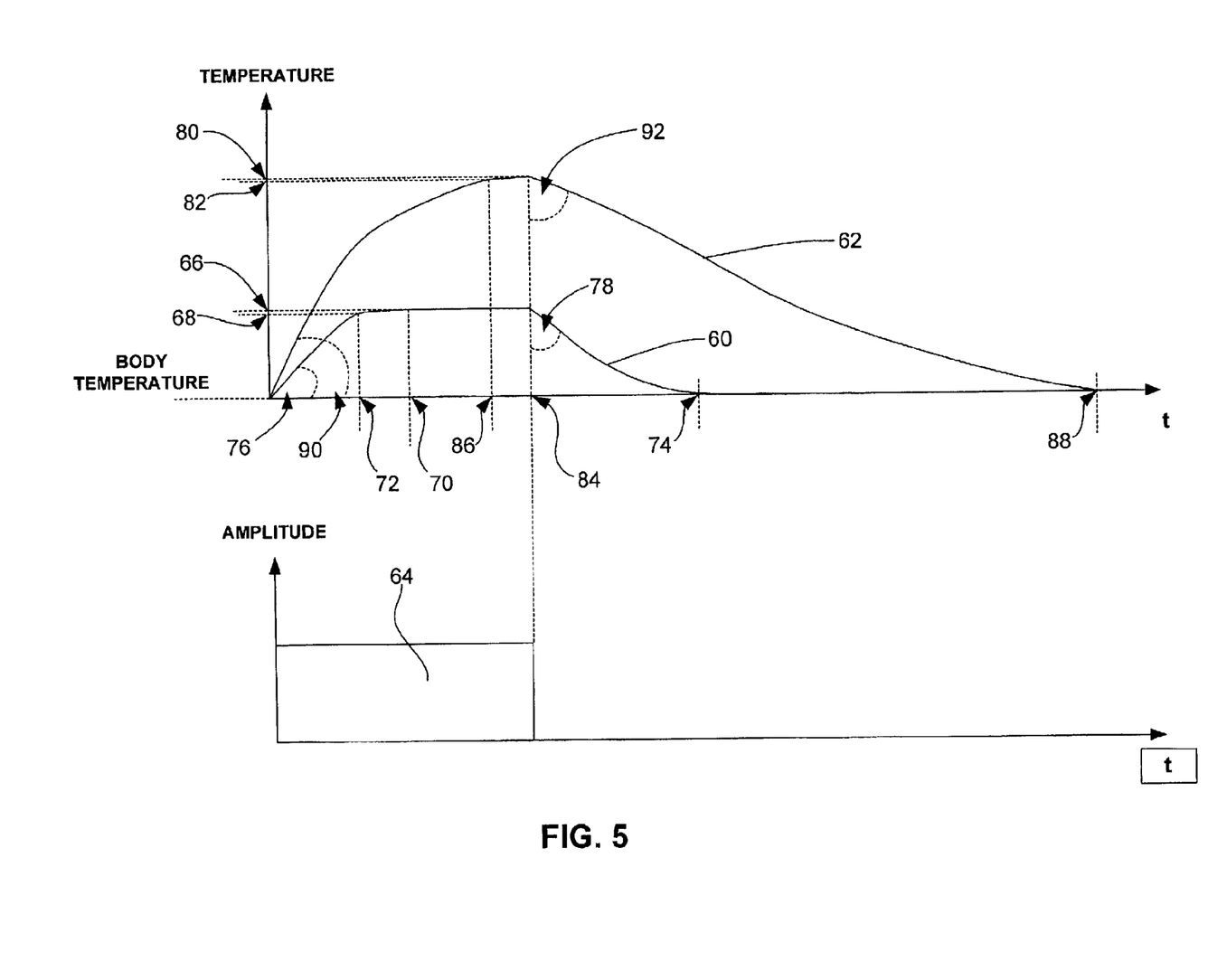
FIG. 5. is a graph illustrating the temperature measured at an ablation electrode, both in the presence and absence of a coagulum, in response to the delivery of RF energy to the ablation electrode.

FIG. 5 shows two curves representative of temperatures that might be measured at an ablation electrode in response to a test RF energy pulse 64. Curve 60 represents the temperatures measured at ablation electrode 30 in the absence of a coagulum. Curve 62 represents the temperatures measured at ablation electrode 30 if a coagulum is present. Both curves start at body temperature, i.e., the temperature measured at the ablation electrode 30 prior to delivery of energy from the ablation electrode, at the time when the test RF energy pulse is delivered. In both cases, the temperature at the ablation electrode will return to body temperature in the absence of further application of energy. In both cases, the temperature at the ablation electrode will increase while the test pulse is delivered, and decrease after delivery is completed. As illustrated by curves 60 and 62, the presence of the coagulum causes the temperature at ablation electrode 30 to increase more quickly, reach a higher peak temperature, and cool more slowly in response to the test pulse.

If pulse 64 is delivered before ablation, curve 60 may represent a baseline temperature response. In order to later determine if coagulum 50 has formed during ablation, one or more characteristics of curve 60 could be measured and the values thereof stored in memory. These characteristics may include, for example, the peak temperature 66, the plateau temperature 68, the time 70 of peak temperature, the time 72 of plateau temperature, the time 74 of the return to body temperature, the slope 76 of the initial temperature increase, the slope 78 of the temperature decrease after pulse delivery has ceased, the mean value of temperature curve 60, or an area under curve 60 determined by integrating the curve between, for example, the time when the pulse delivery begins and the time 74 of the return to body temperature. If test pulse 64 is again delivered after ablation, curve 62 represents the temperature response where a coagulum 50 has formed on ablation electrode 30 during ablation. One or more characteristics of curve 62 can be measured for comparison to the stored baseline values of curve 60 in order to detect the presence of coagulum 50. These characteristics may include, for example, the peak temperature 80, the plateau temperature 82, the time 84 of peak temperature, the time 86 of plateau temperature, the time 88 of the return to body temperature, the slope 90 of the initial temperature increase, the slope 92 of the temperature decrease after pulse delivery has ceased, the mean value of curve 62, or an area under curve 62 determined by integrating the curve between, for example, the time when the pulse delivery begins and the time 88 of the return to body temperature. If coagulum 50 is present, the values of each of the above mentioned characteristics of temperature response curve 62 will be measurably greater than the baseline values of temperature response curve 60. The present invention is not limited to the comparison of the above-mentioned characteristics, but is intended to encompass the comparison of any characteristics of a temperature response curve that would be measurably different when coagulum 50 is present.

Figure 6:
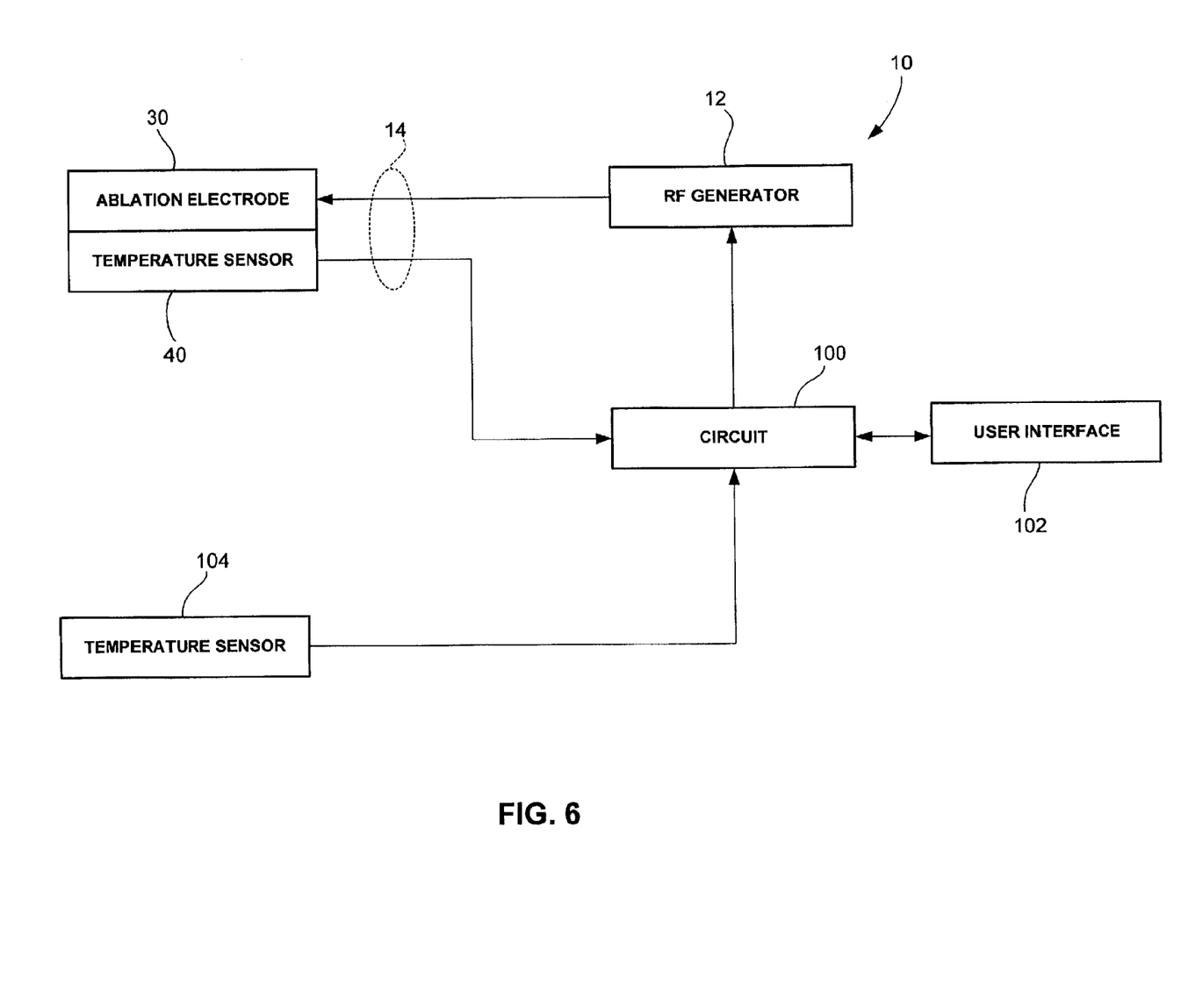
FIG. 6 is a block diagram illustrating a system for ablating tissue according to the present invention.

FIG. 6 illustrates a system for ablating tissue according to the present invention. As shown in FIG. 6, system 10 includes a RF generator 12 which is electrically coupled to ablation electrode 30. Ablation electrode 30 may be carried by catheter 14. Temperature sensor 40 is also located within catheter 14 and is preferably located within or adjacent to ablation electrode 30. Circuit 100 is coupled to temperature sensor 40, to RF generator 12 and to a user interface 102. Circuit 100 may incorporate control circuitry and measurement circuitry.

Temperature sensor 40 measures the temperature at the ablation electrode 30. Circuit 100 receives signals from the temperature sensor 40 that represent the measured temperatures. Circuit 100 may also control the delivery of RF energy by ablation electrode 30 via RF generator 12. Circuit 100 may also receive input from the user and display outputs to the user, particularly outputs indicating the presence or absence of coagulum on the ablation electrode, via user interface 102, which may take the form of a graphic or textual display or other visible or audible output medium, as well as input media such as a keyboard, touchpad, pointing device and the like. Circuit 100 may, for example, be implemented as a microprocessor, ASIC, FPGA, discrete logic circuitry, or analog circuitry, that forms control and measurement functions. Circuit 100 may execute code stored on a variety of media, such as hard disk, optical disk, magnetic tape, removable magnetic disk, or received via a network connection. Circuit 100 may be either a separate device or integral with the RF generator 12.

In an alternative embodiment, system 10 may further include a second temperature sensor 104 coupled to circuit 100. In this embodiment, the second temperature sensor 104 would be located remote from the temperature sensor 40, but still in sensory contact with the patient body so that any variation in the body temperature of the patient during the ablation process may be measured. Temperature sensor 104 may or may not be positioned along catheter 14. This additional temperature sensor 104 is useful for those patients whose body temperature varies during the ablation catheterization procedure. For example, it is sometimes necessary to deliver a drug, such as isoproteronol, to mimic exercise and, in turn, induce arrhythmias. Such a drug, however, often causes the body temperature to rise 1 or 2 degree Celsius. Any change in body temperature during the ablation procedure could be factored in when comparing the temperature responses to test RF pulses delivered before and after ablation.

Figure 7:
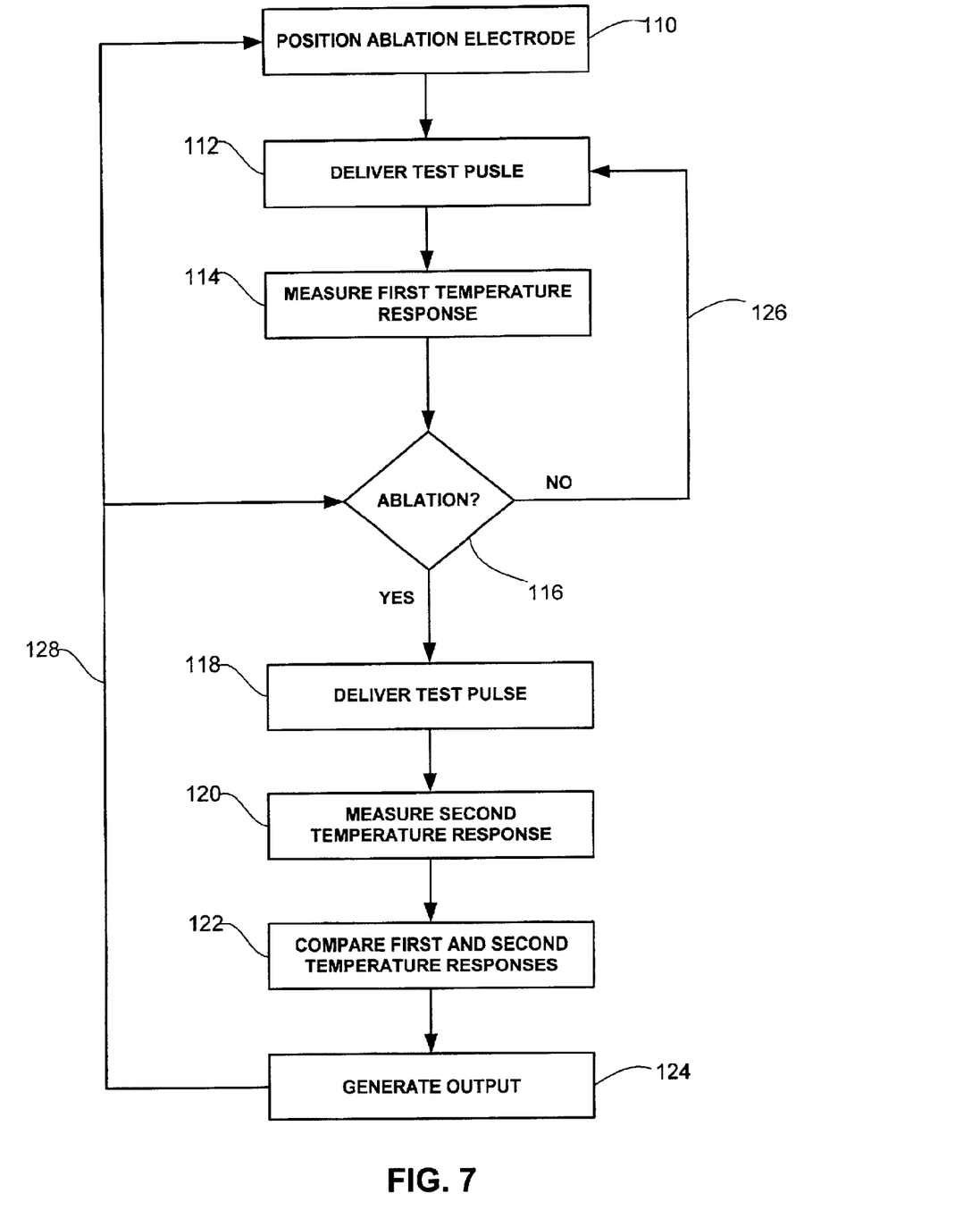
FIG. 7 is a flow diagram illustrating a method of detecting coagulum formation on an ablation electrode during an ablation procedure.

FIG. 7 depicts a method of determining whether a coagulum has formed on an ablation electrode during ablation. A catheter 14 is inserted into the body and preferably into a blood vessel. Catheter 14 preferably has an ablation electrode 30 having a temperature sensor 40. The ablation electrode 30 is coupled to an RF generator 12. A circuit 100, which may be integral with RF generator 12, is coupled to RF generator 12, temperature sensor 40, and user interface 102. Catheter tip 24 is maneuvered such that ablation electrode 30 is at the ablation site (110), i.e., is in contact with the cardiac tissue to be ablated. An RF energy pulse of low power, which is non-damaging to the cellular structures of the body, is supplied to the ablation electrode 30 (112). This low power pulse may be between 0.1 and 1.0 Watts, and may be between 2 and 30 seconds long. This low power pulse serves as a first test pulse. Circuit 100 receives and stores temperature readings from temperature sensor 40 for a period of time after the first test energy pulse is supplied to the ablation electrode 30 (114).

Although not essential to the practice of the present invention, it may be desirable to obtain this baseline temperature response at the ablation site. If the baseline temperature response is measured at a location other than the ablation site, variables other than the presence or absence of coagulum may confound the comparison of temperature responses. In practice, the physician or technician can position the ablation electrode 30 at the ablation site, and then give an indication to the circuit 100 via user interface 102 that the ablation electrode 30 is in position and that the baseline temperature response should therefore be obtained.

Following application of the first test energy pulse (112) and measurement of the baseline temperature response (114), ablation energy is delivered via electrode 30 to cause tissue ablation (116). The physician or technician may, for example, initiate the delivery of ablative RF energy from the RF generator 12 to the ablation electrode 30 by giving an indication to the circuit 100 via user interface 102.

It may be advantageous if the baseline temperature response and the temperature response after ablation are measured close in time. In some embodiments of the present invention, while waiting for the indication that ablation is to begin, the circuit may periodically direct the delivery of repeated test RF energy pulses and receive and store temperature readings (126). This may occur automatically, without any further input from the physician or technician, and will cease when ablation begins. In such an embodiment of the present invention, the baseline temperature response may be the last temperature response received by circuit 100 before ablation. In other embodiments, the baseline temperature response may be calculated based on the average of multiple temperature responses obtained prior to ablation.

After ablation has occurred the RF energy pulse of low power, which is non-damaging to the cellular structures of the body, is again supplied 30 (118). This low power RF pulse serves as a second test pulse. Circuit 100 receives and stores temperature readings from the temperature sensor 40 (120) for a period of time after the RF energy pulse is supplied to the ablation electrode 30. Circuit 100 compares the baseline temperature response measured before ablation to this temperature response measured after ablation to detect whether coagulum has formed at ablation electrode 30 (122).

As described above, if a coagulum 50 has formed around the ablation electrode 30 during ablation, the temperature at the electrode 30 will increase more quickly, reach a higher peak temperature, and cool more slowly in response to the test RF energy pulse. Therefore, circuit 100 could compare any one of, or combination of a number of characteristics of the temperature responses, such as the characteristics described above in reference to FIG. 5, to determine whether a coagulum 50 has formed.

In some embodiments of the present invention, circuit 100 could, for example, determine whether the measured value of a characteristic of the post-ablation temperature response exceeds the baseline value by greater than a threshold percentage. Circuit 100 may indicate the presence of coagulum if the threshold is exceeded. In some embodiments, circuit 100 may measure and compare more than one characteristic. In these embodiments, circuit 100 could, for example, require that two or more percentage thresholds be exceeded before indicating formation of coagulum. Alternatively, circuit 100 may assign weights to each of a number of measured characteristics that are considered together, and determine whether a single threshold percentage is exceeded. A user, such as a physician, may select the threshold values and the weights, and may give them to circuit 100 via user interface 102. The thresholds values and weights may be stored in memory.

In some embodiments, the circuit 100 could also factor the change in a body temperature measurement during ablation into its comparison of the temperature responses. The body temperature could be measured by a second temperature sensor 104.

If the result of the comparison indicates that a coagulum 50 has formed around ablation electrode 30, circuit 100 can generate an appropriate output via the user interface (124). The output could be an audible signal, visual signal, and/or a text message on a display. The output might prompt the physician or technician to remove the catheter 14 and remove the coagulum 50 from the catheter tip 24 and ablation electrode 30. If the result of the comparison indicates that a coagulum 50 has formed, circuit 100 might also prevent further delivery of ablation energy to electrode 30 until the coagulum 50 is removed. An output could also be generated if the result of the comparison indicates no coagulum formation. At that point, the physician or technician could continue ablating at the same site or move the electrode and start the process again (128).

The invention further includes within its scope the methods of making and using the systems described above. These methods are not limited to the specific examples described above, but may be adapted to meet the needs of a particular patient. These and other embodiments are within the scope of the following claims.

What is claimed:

1. A system comprising:
   a temperature sensor to measure temperature at a surgical electrode;
   a power source coupled to the electrode, wherein the circuit controls the power source to deliver energy to the electrode a first and a second time and
   a circuit to compare first and second temperatures measured at the electrode and to indicate the presence or absence of coagulum at the electrode based on the comparison wherein the circuit identifies the first temperature as a temperature measured during the first delivery of energy, and identifies the second temperature as a temperature measured during the second delivery of energy.

2. The system of claim 1, wherein the circuit identifies the first temperature as a peak temperature measured during the first delivery of energy, and identifies the second temperature as a peak temperature measured during the second delivery of energy.

3. The system of claim 1, wherein the circuit calculates the first temperature as an average of temperatures measured subsequent to the start of the first delivery of energy, and calculates the second temperature as an average of temperatures measured subsequent the start of the second delivery of energy.

4. The system of claim 1, wherein the circuit further receives a body temperature value.

5. The system of claim 4, wherein the temperature sensor measures the body temperature value.

6. The system of claim 4, wherein the temperature sensor is a first temperature sensor, the system further comprising a second temperature sensor, wherein the body temperature value is measured by the second temperature sensor.

7. The system of claim 4, wherein the circuit indicates the presence or absence of coagulum based on the comparison of the first and second temperatures and the body temperature value.

8. The system of claim 1, further comprising a catheter, wherein the electrode is disposed at a distal end of the catheter.

9. The system of claim 1, wherein the temperature sensor is located within the electrode.

10. The system of claim 1, wherein the temperature sensor includes one of a thermistor and a thermocouple.

11. The system of claim 1, wherein the power source delivers energy via the electrode at a level that is substantially non-damaging to cellular structures of human blood cells and human cardiac tissue.

12. The system of claim 1, wherein the power source delivers RF energy at a level that is within the range from 0.1–1.0 Watts.

13. The system of claim 1, wherein the circuit controls the power source to deliver energy to the electrode at a level sufficient to cause ablation of cardiac tissue between the first time and the second time.

14. A system comprising:
- a temperature sensor to measure temperature at a surgical electrode; and
- a circuit to compare first and second temperatures measured at the electrode and to indicate the presence or absence of coagulum at the electrode based on the comparison wherein the circuit receives a threshold value, compares a result of the comparison of the first and second temperature to the threshold value, and indicates the presence or absence of coagulum based on the comparison of the result to the threshold value.

15. The system of claim 14, wherein the circuit generates an output based on the comparison, the output being one of an audible indicator, a visual indicator, and a text message on a display.

16. A system comprising:
- a temperature sensor to measure temperatures at a surgical electrode;
- a power source coupled to the electrode;
  - controls circuitry that controls the power source to deliver energy to the electrode a first and second time; and
- measurement circuitry that compare first and second temperatures measured at the electrode, and indicates the presence or absence of coagulum at the electrode based on the comparison, wherein the measurement circuitry measures a first time interval from a time when the first delivery of energy begins to a time when a first temperature is measured at the electrode, measures a second time interval from a time when the second delivery of energy begins to a time when a second temperature is measured at the electrode, compares the first and second time interval, and indicates the presence or absence of coagulum at the electrode based on the comparison.

17. The system of claim 16, wherein the measurement circuitry receives a threshold value, compares a result of the comparison of the first and second time intervals to the threshold value, and indicates the presence or absence of coagulum based on the comparison of the result to the threshold value.

18. The system of claim 16, wherein the measurement circuitry identifies the first temperature as a peak temperature measured during the first delivery of energy, arid identifies the second temperature as a peak temperature measured during the second delivery of energy.

19. The system of claim 16, wherein the measurement circuitry measures a first time interval from a time when the first delivery of energy ends to a time when a first temperature is measured at the electrode, measures a second time interval from a time when the second delivery of energy ends to a time when a second temperature is measured at the electrode, compares the first and second time interval, and indicates the presence or absence of coagulum at the electrode based on the comparison.

20. The system of claim 19, wherein the measurement circuitry receives a threshold value, compares a result of the comparison of the first and second time intervals to the threshold value, and indicates the presence or absence of coagulum based on the comparison of the result to the threshold value.

21. A system comprising:
- a temperature sensor to measure temperatures at a surgical electrode and generate a temperature signal as a function of the temperatures;
- a circuit to measure a first and second slope of the temperature signal, to compare the first and second slope, and to indicate the presence or absence of coagulum at the electrode based on the comparison; and
- a power source coupled to the electrode, wherein the circuit controls the power source to deliver energy to the electrode a first and a second time, wherein the circuit measures the first slope during the first delivery of energy, and measures the second slope during the second delivery of energy.

22. The system of claim 21, wherein the circuit measures the first slope subsequent to the first delivery of energy, and measures the second slope subsequent to the second delivery of energy.

23. The system of claim 21, wherein the circuit receives a threshold value, compares a result of the comparison of the first and second slope to the threshold value, and indicates the presence or absence of coagulum based on the comparison of the result to the threshold value.

24. A system comprising:
- a temperature sensor to measure temperatures at surgical electrode and generate a temperature signal as a function of the temperatures; and
- a circuit to integrate the temperature signal and to indicate the presence or absence of coagulum at the electrode as a function of a result of the integration, wherein the circuit controls a power source to deliver energy to the electrode a first and second time, integrates the temperature signal from a time when the first delivery of energy begins to a time when a first temperature is measured at the electrode, integrates the temperature signal from a time when the second delivery of energy begins to a time when a second temperature is measured at the electrode, compares a result of integrating the temperature signal from the time when the first delivery of energy begins to the time when a first temperature is measured at the electrode to a result of integrating the temperature signal from the time when the second delivery of energy begins to the time when the second temperature is measured, and indicates the presence or absence of coagulum at the electrode based on the comparison.

25. The system of claim 24, wherein the circuit receives threshold value, compares a result of the comparison between the two integration results to the threshold value, and indicates the presence or absence of coagulum based on the comparison of the result to the threshold value.

* * * * *